(12) United States Patent
Walker

(10) Patent No.: US 6,453,183 B1
(45) Date of Patent: Sep. 17, 2002

(54) CEREBRAL OXYGENATION MONITOR

(76) Inventor: Stephen D. Walker, 1472 Cassin Ct., Boulder, CO (US) 80303

( * ) Notice: Subject to any disclaimer, the term of this patent is extended or adjusted under 35 U.S.C. 154(b) by 0 days.

(21) Appl. No.: 09/545,916

(22) Filed: Apr. 10, 2000

(Under 37 CFR 1.47)

(51) Int. Cl.[7] .................................................. A61B 5/00
(52) U.S. Cl. ......................... 600/322; 600/323; 600/338
(58) Field of Search ................................ 600/309–310, 600/322–328, 340, 338; 356/39–41

(56) References Cited

U.S. PATENT DOCUMENTS

| | | | | | |
|---|---|---|---|---|---|
| 5,413,100 | A | * | 5/1995 | Barthelemy et al. | 600/328 |
| 5,440,388 | A | * | 8/1995 | Erickson | 356/456 |
| 5,553,615 | A | * | 9/1996 | Carim et al. | 600/324 |
| 5,608,519 | A | * | 3/1997 | Gourley et al. | 356/318 |
| 5,782,237 | A | * | 7/1998 | Casciani et al. | 600/476 |
| 5,995,856 | A | * | 11/1999 | Mannheimer et al. | 600/322 |
| 5,995,857 | A | * | 11/1999 | Toomim et al. | 600/322 |
| 6,195,575 | B1 | * | 2/2001 | Levinson | 600/338 |
| 6,253,097 | B1 | * | 6/2001 | Aronow et al. | 600/310 |

OTHER PUBLICATIONS

S.N. Jarvis, J.S. Holloway, E.N. Hey "Increase in cerebral palsy in normal birthweight babies," Arch Dis Child 60, 1113–1121 (1985).

D.M. Eddy, J. Billings "The quality of medical evidence: Implications for quality of care," Health Aff 7(1), 19–32 (1988).

K.B. Nelson, J.H. Ellenberg "Antecedents of cerebral palsy: multivariate analysis of risk," N Engl J Med 315, 81–86 (1986).

K.R. Nelson, J.M. Dambrosia, T.Y. Ting, J.K. Grether "Uncertain value of electronic fetal monitoring in predicting cerebral palsy," N Engl J Med 334(10), 613–618 (1996).

A.M. Vintzileos MD, A. Antsaklis MD, I. Varvarigos MD, C. Papas MD, I. Sofatzis MD, J.T. Montgomery RN "A randomized trial of intrapartum electronic fetal heart rate monitoring versus intermittent auscultation,"Obstet Gynecol 81(6), 899–907 (1993).

L.L. Albers, C.J. Krulewitch "Electronic fetal monitoring in the United States in the 1980s,".

A. Elimian MD, R. Figueroa MD, N. Tejani MD "Intrapartum assessment of fetal well–being: A comparison of Scalp Stimulation with Scalp Blood pH sampling," Obstet Gynecol89, 373–376 (1997).

T.R.B. Johnson MD, M.J. Johnson MD, M.J. Johnson MD "Identifying fetal movement and behavior patterns," Contemp Ob/Gyn Sep. 11–16 (1993).

Luttkus AK Dudenhausen JW, Fetal pulse oximetry, Current Opinion in Obstetrics and Gynecology, 11:481–488, 1998.

Faiss K et al, Intrapartum reflectance pulse oximetry: effects of sensor location and fixation duration on oxygen saturation readings, J Clin Mon, 13:299–302, 1997.

G.A. Dildy MD, J.A. Tnorp MD, J.D. Yeast MD, S.L. Clark MD, "The relationship between oxygen saturation monitoring," Am J Obstet Gynecol 175(3), 682–687 (1996).

(List continued on next page.)

Primary Examiner—Eric F. Winakur
Assistant Examiner—Matthew Kremer
(74) Attorney, Agent, or Firm—Gibson, Dunn & Crutcher LLP

(57) ABSTRACT

A method and apparatus for determining oxygenation and hemoglobin parameters in tissue measures light scattering parameters of light directed through the tissue, using an array of VCSELs, for light directed at more than one frequency. This allows for the calculation of Hb, $HbO_2$, and other parameters.

7 Claims, 3 Drawing Sheets

OTHER PUBLICATIONS

S. Lurie, A. Weissman, G. Blumberg, Z. Hagay, "Fetal oximetry monitoring: A new wonder or another mirage" Obstet Gynecol 51(8), 498–502 (1996).

M.S. Patterson, J.D. Moulton, B.C. Wilson, K.W. Berndt, J.R. Lakowicz, "Frequency–domain reflectance for the determination of the scattering and absorption properties of tissue," Appl. Opt. 30, 4474–4476 (1991).

W.J. Levy, S. Levin, B. Chance, "Near–infrared Measurement of Cerebral Oxygenation," Anesthesiology, 83, 738–746 (1995).

Firbank M Motoki O Delpy D, "An improved design for a stable and reproducible phantom material for use in near–infrared spectroscopy and imaging," Phys Med Biol 40 955–961, 1995.

Yodh A Chance B, Spectroscopy and Imaging with Diffusing Light, Physics Today, pp. 34–40, Mar. 1995.

Arridge, S.R., Cope, M., Delpy, D.T., "The theoretical basis for the determination of optical pathlengths in tissue: temporal and frequency analysis," "Phys. Biol. Med." *37*, 1531–1560, 1992.

Kohl, M., Watson, R., and Cope, M., "Phase and Modulation Depth," Proceedings of SPIE, vol. 2979, pp. 365–374, 1997.

Patterson, M., Chance, B., Wilson, B.C., *Applied Optics 28*, 2331–2336, 1989.

Noika, S., Yung, Y., Shnall, M., Zhao, S., Orel, S, Xie, C., Chance, B., and Solin, L. in *Oxygen Transport to Tissue VIII*, pp. 227–232, 1997.

\* cited by examiner

CEREBRAL OXYGENATION MONITOR

FIELD OF THE INVENTION

The present invention relates to a method and apparatus for monitoring cerebral oxygenation (i.e., a Cerebral Oxygenation Monitor or COM), particularly in the intrauterine environment. The method includes measuring light scattering parameters of light directed through the cerebral cortex.

BACKGROUND

Fetal brain injury resulting from hypoxia and ischemia during labor is an important cause of death and long-term disability. However, little is known about fetal brain oxygenation and hemodynamics because there are currently no satisfactory clinical techniques for fetal monitoring. There is a need for a new method to assess fetal deep brain oxygenation.

With the United States experiencing unacceptably high infant mortality rates, national health objectives have targeted reductions in infant mortality, fetal death, low birth weight, and severe complications of pregnancy, along with reduction in severe mental retardation, as important goals to be achieved in this decade. However, the attainment of these goals has remained elusive, even with the rising cost of health care.

Obstetrical care continues to be more technology oriented than many other areas of health care. Risk factors are quickly identified, and patients are followed with an array of tools including electronic fetal monitoring (EFM), ultrasound, amniocentesis, and laboratory tests which were virtually unknown 20 years ago. Yet perinatal morbidity and mortality have not yielded to this intensive investment of resources. At least one form of neurologic handicap (cerebral palsy) may be on the rise. An example of perhaps the most obvious unintended and undesirable consequence of the use of surveillance methods has been the drastic increase in the cesarean delivery rate. While the rate is falling, there is still general agreement that the rate is too high and should be lowered if possible. In fact, the national health objectives now include a targeted reduction in the cesarean delivery rate.

As indicated, increasing expenditures for perinatal care have not led to a corresponding reduction in infant mortality, low birth weight deliveries, severe mental retardation, or birth defect rates in the United States. A principal explanation for this lack of progress is the scientific uncertainty surrounding the provision of perinatal care. Significant variation in the practice of medicine, and concomitant variation in health care costs, arise when there is insufficient scientific knowledge to support one alternative over another. Such is the case with the most feared aspect of perinatal morbidity: neurologic handicap, principally cerebral palsy, but also including mental retardation, learning disabilities and epilepsy. For over 100 years, the medical profession has assumed that the circumstances of birth predict which infants will develop cerebral palsy. Until recently, rigorous analyses had failed to confirm this assumption. A recent comprehensive review concluded that it is not possible to predict which babies are at risk for brain disorders and which of the at-risk babies will actually experience problems. Although a 1996 study found that there was an association between abnormal findings on EFM and the risk of cerebral palsy, the false-positive rate was very high.

Regrettably, there is currently no highly sensitive and specific technology to assess fetal well being. Therefore, a method that accurately and reliably categorizes fetal status has the potential to significantly improve perinatal outcomes while managing health care costs.

Intrapartum fetal evaluation is used to prevent neonatal illness and death as well as intrapartum fetal death. Intermittent auscultation was originally utilized for this purpose, and remains acceptable for monitoring "low risk" patients. EFM subsequently was touted as a method of evaluation that would lead to decreased cerebral palsy, neonatal and intrapartum death rates. Although it places less of a demand on nursing staff, allows continuous and objective recording of information (fetal and uterine), and allows improved detection of patterns of fetal distress that are missed by auscultation, its benefit over no monitoring has not been proven.

Fetal heart rate patterns of distress may be associated with fetal acidemia, hypoxemia and acidosis. Abnormal fetal heart rate patterns, although a good predictor of fetal distress, are not good predictors of cerebral palsy. EFM is reassuring when normal. When abnormal, correct diagnosis of the problem requires an attendant skilled in EFM interpretation and ancillary procedures such as fetal scalp stimulation and scalp pH monitoring, vibroacoustic stimulation, ultrasound, etc.

The drawback in these methods is that they do not provide a direct assessment of fetal brain oxygenation, which is ultimately the most important variable in determining whether an infant will suffer from long-term neurologic injury or succumb to death. A method of fetal evaluation for those infants with a distress pattern that would allow detection of cerebral hypoxia is needed. The EFM is a screening test. The diagnostic tests detailed above have lead to increasing cesarean section rates with no reduction in cerebral palsy and a minimal reduction in intrapartum death.

A testing modality that would allow clinicians a more direct method of evaluating cerebral oxygenation would target the hypoxic fetus and thus reduce the number of unnecessary cesarean sections performed for the misperception of "fetal distress," and in turn decrease maternal morbidity and mortality, as well as length of hospital stay and, thus, lower medical costs.

An instrument according to different aspects of the present invention addresses at least three different clinical needs. The first is continuous non-invasive monitoring of fetal cerebral oxygenation during labor and delivery. This requires a small, unobtrusive, bedside instrument.

A second aspect of the invention is a postpartum imager. The imager has a position sensor on the probe and a high resolution video display. Images will resemble diagnostic ultrasound B-scans. The technology used in the postpartum imager utilizes identical laser light sources, detectors and signal processing as the COM. A three dimensional image is produced by overlaying many individual COM readings taken from different volumes of the newborn head on a display. The different sample volumes can be obtained in two ways. First, a source-detector pair can be positioned at different locations on the head similar to an ultrasound B-scan. Alternatively, an array of source-detector pairs can take a sequence of sample volumes similar to computed tomography.

The third aspect of the invention is an antepartum monitor. Because the instrument can penetrate 8–10 cm of tissue, fetal cerebral oxygenation images can be obtained through the mothers abdomen. The principle of the antepartum imager is identical to the postpartum imager. The specially conditioned laser light penetrates the additional soft tissue of the mother and the same banana shaped sample volume is measured. Roughly 50% of the middle of the sample volume is fetal cerebral tissue. Fetal tissue is differentiated from maternal tissue on the resulting three dimensional image by the dark outline of the fetal skull.

Comparison of the Present Invention with Fetal Pulse Oximeters

Fetal pulse oximeters have been in development for several years. This device utilizes a modification of adult finger probe transmission technology to perform reflectance pulse oximetry on intrauterine fetal cheeks. The probe is attached to the fetal cheek and held in place by pressure from the uterine wall. However, investigators outside of the United States have been evaluating fetal pulse oximeters for several years and conclude that the current generation of fetal pulse oximetry sensors is not improving the quality of combined monitoring of fetal heart rate and fetal scalp blood analysis. This is not the case for a COM according to the present invention as shown in the following comparison with the fetal pulse oximeter.

| Feature | COM | Fetal Pulse Oximeter |
| --- | --- | --- |
| Type | Near Infrared Laser Spectrometer | Reflectance Pulse Oximeter |
| Measured Parameters | PO2, O2 Saturation | Arterial Saturation |
| Location | Fetal Cerebral Tissue | Fetal Cheek |
| Hair Penetration | Yes | No |
| Attachment Method | Mild Suction | None |

COM is a near infrared spectrometer (NIRS) that uses laser diodes for the optical source. Laser diodes have adequate power at a specific wavelength to penetrate fetal hair, scalp, and skull into deep gray and white matter, while remaining comfortably within the safety standards. Fetal pulse oximeters use LEDs for optical sources that emit a weaker broad spectrum light beam. The significance of the difference in optical source lies in the ability of COM to measure the lower cerebral tissue oxygenation rather than the cheek saturation measured with fetal oximeters. A second difference is that the COM intrauterine probe is held in place by suction, which has been shown to effectively maintain contact.

Spectrometers

The analysis of absorption and scattering properties of deep brain tissue is an important problem in fetal and neonatal health, in particular for determining chromophore concentrations in tissue of hemoglobin (Hb), oxyhemoglobin ($HbO_2$) and cytochrome oxidase. Conventional near infrared spectrometers (NIRS) allow the changes in chromophore concentrations to be calculated from changes in the light intensity diffusely reflected from the tissue surface. However, the absolute concentrations of these chromophores, i.e. the absolute absorption coefficient, cannot easily be inferred as the scattering of the light in the tissue must be taken into account.

The following documents include information generally related to the present invention, and are all incorporated in their entirety by reference:

1. U.S. Department of Health and Human Services. "Healthy People 2000: national health promotion and disease prevention objectives," DHHS Publication No. (PHS) 91-50212. Washington, U.S. Government Printing Office, 368–377 (1991).
2. Health U.S., U.S. Department of Health and Human Services, Washington, D.C. (1995).
3. S. N. Jarvis, J. S. Holloway, E. N. Hey "Increase in cerebral palsy in normal birthweight babies," Arch Dis Child 60, 1113–1121 (1985).
4. S. F. Bottoms, M. G. Rosen, R. J. Sokol "The increase in the cesarean birth rate," N Engl J Med 320, 559–563 (1980).
5. Consensus Development Conference. Cesarean Childbirth. NIH Publication No. 82-2067. Bethesda, Maryland, National Institutes of Health (1981).
6. D. M. Eddy, J. Billings "The quality of medical evidence: Implications for quality of care," Health Aff 7(1), 19–32 (1988).
7. W. J. Little "On the influence of abnormal parturition, difficult labours, premature birth, and asphyxia neonatorum, on the mental and physical condition of the child, especially in relation to deformities," Trans Obstet Soc London 3, 191–344 (1962).
8. K. B. Nelson, J. H. Ellenberg "Antecedents of cerebral palsy: multivariate analysis of risk," N Engl J Med 315, 81–86 (1986).
9. J. M. Freeman ed "Prenatal and perinatal factors associated with brain disorders," NIH Publication No. 85-1149. Washington, U.S. Department of Health and Human Services (1985).
10. K. R. Nelson, J. M. Dambrosia, T. Y. Ting, J. K. Grether "Uncertain value of electronic fetal monitoring in predicting cerebral palsy," N Engl J Med 334(10), 613–618 (1996).
11. A. M. Vintzileos MD, A. Antsaklis MD, I. Varvarigos MD, C. Papas MD, I. Sofatzis MD, J. T. Montgomery RN "A randomized trial of intrapartum electronic fetal heart rate monitoring versus intermittent auscultation," Obstet Gynecol 81(6), 899–907 (1993).
12. L. L. Albers, C. J. Krulewitch "Electronic fetal monitoring in the United States in the 1980s," Obstet Gynecol 82, 8–10 (1993).
13. A. Elimian MD, R. Figueroa MD, N. Tejani MD "Intrapartum assessment of fetal well-being: A comparison of Scalp Stimulation with Scalp Blood pH sampling," Obstet Gynecol 89, 373–376 (1997).
14. T. R. B. Johnson MD, M. J. Johnson MD "Identifying fetal movement and behavior patterns," Contemp Ob/Gyn 11–16 September (1993).
15. Luttkus A K Dudenhausen J W, Fetal pulse oximetry, Current Opinion in Obstetrics and Gynecology, 11:481–488, 1998.
16. Faiss K et al, Intrapartum reflectance pulse oximetry: effects of sensor location and fixation duration on oxygen saturation readings, J Clin Mon, 13:299–302, 1997.
17. Cope, D. T Delpy "A system for the long-term measurement of cerebral blood and tissue oxygenation in newborn infants by near-infrared transillumination," Med. Biol. Eng. Comput. 26, 289–294 (1998).
18. G. A. Dildy MD, J. A. Tnorp MD, J. D. Yeast MD, S. L. Clark MD "The relationship between oxygen saturation and pH in umbilical blood: Implications for intrapartum fetal oxygen saturation monitoring," Am J Obstet Gynecol 175(3), 682–687 (1996).
19. S. Lurie, A. Weissman, G. Blumberg, Z. Hagay "Fetal oximetry monitoring: A new wonder or another mirage?" Obstet Gynecol 51(8), 498–502 (1996).
20. S. J. Matcher, P. Kirkpatrick, K. Nahid, M.Cope, D. T. Delpy "Absolute quantification methods in tissue near-infrared spectroscopy," SPIE Proceeding 2389, Optical tomography, photon migration, and spectroscopy of tissue and media: theory, human studies, and instrumentation, 486–495 (1995).
21. M. S. Patterson, J. D. Moulton, B. C. Wilson, K. W. Berndt, J. R. Lakowicz "Frequency-domain reflectance for the determination of the scattering and absorption properties of tissue," Appl. Opt. 30, 4474–4476 (1991).

22. B. J. Tromberg, L. O. Svaasand, T. T. Tsay, R. C. Haskell "Properties of photon density waves in multiple-scattering media," Appl. Opt. 32, 607–616 (1993).
23. M. Kohl, R. Watson, M. Cope "Determination of absorption coefficients in highly scattering media from changes in attenuation and phase," Optics Let., 21, 1519–1521 (1996).
24. M. S. Patterson, B. Chance, B. C. Wilson "Time resolved reflectance and transmittance for the non-invasive measurement of tissue optical properties," Appl. Opt. 28, 2331–2336 (1989).
25. S. Arridge, M. Cope, D. T. Delpy, "The theoretical basis for the determination of optical pathlengths in tissue: temporal and frequency analysis," Phys. Med. Biol. 37, 1531–1560 (1992).
26. W. J. Levy, S. Levin, B. Chance, "Near-infrared Measurement of Cerebral Oxygenation," Anesthesiology, 83, 4 (1995).
27. Firbank M Motoki 0 Delpy D Phys Med Biol 40 955–961, 1995.
28. Hebden, Tziraki, Delpy, Applied Optics vol 36, 3802–3810, 1997.
29. Bohren CF Huffhian DR Absorption and Scattering of Light by Small Particles, New York, Wiley, 1983.
30. Yodh A Chance B, Spectroscopy and Imaging with Diffusing Light, Physics Today, ppg 34–40, March 1995.

None of the above documents are admitted to anticipate or render obvious in any combination the present invention, but are included to help place the present invention in context.

SUMMARY

A method and apparatus for determining the total hemoglobin and saturation, and absolute Hb and $HbO_2$ concentrations are provided. Total hemoglobin is the sum of all the different types of hemoglobin. Hb concentration is the amount of deoxygenated blood and HbO2 concentration indicates how much oxygenated blood is present. The significance of absolute HbO2 concentrations is it quantifies the amount of oxygen in the tissue. Significant concentrations of Hb indicates the tissue is not being oxygenated properly. Absolute hemoglobin concentrations quantify the amount of hemoglobin and oxygen is tissue.

The measurement of these parameters provides significantly more information than Saturation, the ratio of HbO2 to total hemoglobin. The Saturation ratio does not indicate how much hemoglobin or oxygen is present. An instrument according to the present invention is significantly less complex than conventional near infrared spectrometers, because it measures slight changes in tissue absorption produced by small optical source wavelength changes. In a preferred application, the instrument gives an early-warning of cerebral injury through intrauterine monitoring. The instrument will also lower the cost of health care delivery because it is estimated that 25%–35% of all C-sections could be avoided with the monitoring capability provided by the invention.

In a preferred application, a probe is placed over a fetal scalp for probing through the skull into the cortex. Probe components include the probe body containing a light source, common detector, and a cable leading from the probe body to the monitor. The probe body consists of a flexible circuit with electrical contacts for the detector and cable. The flexible circuit is preferably encapsulated in an optical grade silicon which allows the probe to conform to the curvature of the skull. Light passes through the cortex in a banana shaped path from the light source to the common detector. Reflected light is measured at the detector, amplified and transmitted via the cable to the monitor. It should be apparent that one or more sources and one or more detectors could be used in any combination, and that in the invention as claimed a reference to "a detector" will be construed to include more than one detector and a reference to multiple detectors will be construed to include one detector operating a multiple wavelengths.

The cerebral oxygenation monitor (COM) according to the present invention allows evaluation of deep gray and white matter of the fetal brain, and measures brain tissue saturation, Hb and $HbO_2$. This is an improvement over the new fetal pulse oximeters (which measure arterial saturation) at an equivalent cost. The COM is a diagnostic test that is in one embodiment noninvasive to the fetus (rupture membranes required for its placement) to be used in those patients where EFM suggests the fetus is at risk. The parameters measured may provide vital information including: evaluation of "fetal distress" patterns—knowing brain tissue oxygen saturation will more precisely determine whether the fetus is at true risk of long-term neurologic injury or death; and evaluation of total hemoglobin—in infants anemic due to iso-immunization or vasa previa, possible conservative management of their delivery could be allowed. The COM thus is of great potential value in obstetrics. Intermittent and continuous use of its parameters in the "at risk" fetus may facilitate an improvement in fetal and maternal health.

Optimal Spectroscopic Source: Vertical Cavity Surface Emitting Lasers

The COM may utilize vertical cavity surface emitting laser (VCSEL) optical sources that have many important advantages over other types of lasers. A VCSEL approach may be selected for COM because: VCSELs are inherently much simpler than other optical source systems; the emission wavelength of VCSELs is controlled by temperature rather than a mechanical system; VCSELs are small and low cost because they are manufactured with bulk semiconductor technology; VCSELs can be attached directly to the fetal head rather than through a fiber; VCSELs are low power but can be built in arrays that meet the power requirements to penetrate fetal hair and bone; and VCSELs at different wavelengths can be placed on the same probe. In this manner, an aspect of the invention includes simultaneously measuring at two wavelengths, such as 760 nm and 830 nm, wherein both arrays are mounted in a single fetal probe. The use of VCSELs is a system similar to the disclosed system is believed to be unknown in the prior art, and represents an important technical advance.

Technical Rationale

Different experimental approaches have been developed for the measurement of absolute absorption coefficients ($\mu_a$) and scattering coefficients ($\mu_s'$), in highly scattering media. Reflected intensity measurements for different distances between light source and detector can be used. Alternatively, measurements can be based upon the time of flight of the light in tissue in addition to the reflectance. Intensity modulated laser spectrometers (IMLS) are an alternative to time resolved systems, and provide measurements of the phase and the modulation depth of an intensity modulated light wave. The phase difference is approximately proportional to the mean time of flight of the light in the medium. It has been shown that, for a fixed modulation frequency, $\mu_a$ and $\mu_s'$ can be inferred from the intensity and phase data obtained at different source detector distances. Alternatively, single distance, multiple modulation frequency measurements can be used. All of these methods are based upon fitting $\mu_a$ and $\mu_s'$ to diffusion equation solutions for light transport in the medium.

The present invention includes a method for the determination of absorption coefficients. The basic premise is that small changes in the absorption coefficient induce changes in diffuse light intensity, phase, and modulation depth, and that the ratio of these changes is primarily independent of the scattering properties of the medium. This ratio provides a good estimate of the absolute absorption coefficient. The approximation is only valid over a certain range of $\mu_a$ and $\mu_s'$ values, however it encompasses the range found in biological tissues for near infrared wavelengths. Similarly, the ratio of the changes in intensity and phase, induced by variation in the source wavelength, allows $\mu_a$ to be estimated. Furthermore, $\mu_s'$ can be inferred based upon the estimated $\mu_a$ value. The main advantages of the suggested method for the in vivo monitoring of hemoglobin concentration and oxygen saturation is its simplicity. Source-detector distance remains constant, there is no expensive time-of-flight instrumentation and no multiple modulation schemes.

DETAILED DESCRIPTION

Overview

Figure 1:
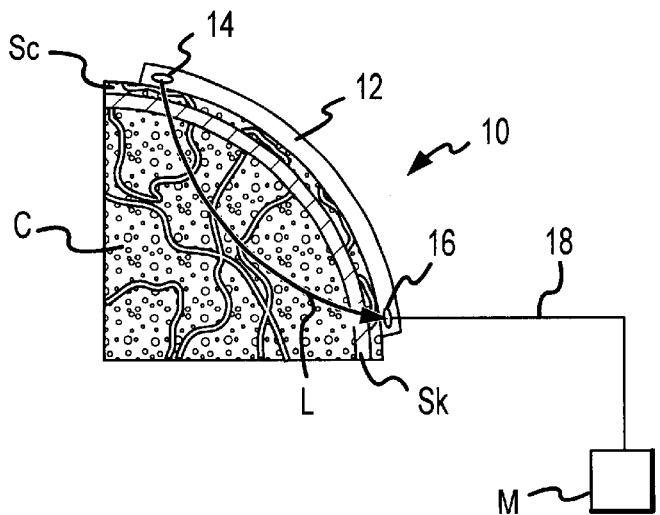
FIG. 1 is a schematic representation of an overview of a probe system according to an aspect of the invention.

A schematic representation of an intrauterine probe apparatus according to the present invention is shown in FIG. 1. This diagram shows the fetal cortex C, skull Sk and scalp Sc. A probe 10 has components including a probe body 12 containing a light source 14, a common detector 16 and a cable 18 to a monitor M. The probe body 12 consists of a flexible circuit with electrical contacts for the detector 16 and cable 18. The flexible circuit is encapsulated in an optical grade silicon which allows the probe to conform to the curvature of the skull. The dotted line L through the cortex C is one possible light path from the light source 14 to the common detector 16. Reflected light is measured at the detector 16, amplified and transmitted via the cable 18 to the monitor M.

Operating Principles

While the applicant believes that the principles that govern the operation of the present invention are understood as set forth below and elsewhere herein, it should be understood that the utility of the invention has been experimentally verified and the applicant is not bound by any scientific theory to the extent the principles herein are in any way incorrect or incomplete, as the operation of a device according to the present invention as been verified.

The transport of light in scattering media has been analyzed over recent years and diffusion theory has become established as a versatile tool for describing light intensity, time of flight, phase and modulation depth in terms of the scattering coefficient ($\mu_s'$), the absorption coefficient ($\mu_a$) and the refractive index of the medium (n). For a laser light source on a semi-infinite halfspace, the reflectance R (the number of photons back scattered to the surface of the medium per unit area) and the mean transit time (time of flight) $<t>$ detected at a distance r from the source can be written as $$R(r) = z_0 \cdot \left(\frac{1}{\rho} + \mu_{eff}\right) \cdot \frac{\exp(-\mu_{eff} \cdot \rho)}{2\pi \cdot \rho^2}, \quad \text{Equation 1}$$

and $$\langle t \rangle(r) = \frac{\rho^2}{2c \cdot (D + \rho \cdot \sqrt{\mu_a \cdot D})}. \quad \text{Equation 2}$$

It is assumed that the laser beam creates an isotropic photon source at depth $z_0$. In Eqns. 1 and 2, $\rho = (r^2 + z_0^2)^{1/2}$ and $z_0 = 1/\mu_s'$. The velocity of light in the medium $c = c_0/n$ (where $c_0$ is the speed of light in vacuum), $\mu_{eff} = (3\mu_a(\mu_a + \mu_s'))^{1/2}$ is the effective attenuation coefficient and $D = (3(\mu_a + \mu_s'))^{-1}$ is the diffusion coefficient. When an intensity modulated optical spectrometer is employed to measure chromophore concentration, the phase $\phi$ of a laser beam, intensity modulated at the frequency $v_M$, is measured rather than the mean time. $\phi$ and $<t>$ are approximately coupled by the simple linear relationship $$\phi = -2\pi \cdot v_M \cdot <t>, \quad \text{Equation 3}$$

which is valid for the range of n, $\mu_a + \mu_s'$ values typical for tissue at NIR wavelengths and frequencies $v_M < 200$ MHz. Analytical expressions for the phase $\phi$ and the modulation depth M (the ratio of the AC and DC components of the modulated laser beam) are derived by performing a Fourier transformation of the temporal resolved impulse response of the reflectance R(r,t) to give $$\phi = \psi_r - \tan^{-1}\left(\frac{\psi_r}{1 + \psi_i}\right) \quad \text{Equation 4}$$

and $$M = \frac{\sqrt{1 + \psi_0^2 + 2\psi_i}}{1 + \psi_\infty} \cdot \exp(\psi_\infty - \psi_i) \quad \text{Equation 5}$$

where $\psi_0 = \mu_{eff} \cdot \rho \cdot [1 + \chi^2]^{1/4}$, $\psi_r = -\psi_0 \cdot \sin(\theta/2)$, $\psi_i = \psi_0 \cdot \cos(\theta/2)$, $\theta = \tan^{-1}(\chi)$, $\psi_\infty = \mu_{eff} \cdot \rho$ and $\chi = (2\pi v_M)/(\mu_a c)$. The derivative of the attenuation A (log of the incident and detected intensity) and $<t>$ with respect to changes in $\mu_a$ can be derived from Eqn 1 and 2 giving $$\frac{\partial A}{\partial \mu_a} = \frac{3}{2\ln 10} \cdot \frac{\rho}{1/\rho + \mu_{eff}} \cdot (2\mu_a + \mu_s') \quad \text{Equation 6}$$

and $$\frac{\partial \langle t \rangle}{\partial \mu_a} = \frac{-3}{2(1/\rho + \mu_{eff})^2 \cdot c} \cdot \left[\frac{\rho}{2} \cdot \frac{\mu_s'}{\sqrt{\mu_a \cdot D}} - 1\right]. \quad \text{Equation 7}$$

The quotient $Q_a = (\partial A/\partial \mu_a)/(\partial \phi/\partial \mu_a)$ can be simplified by using the diffusion approximation which states that scattering dominates absorption when $(\mu_a << \mu_s')$, $\mu_{eff} \cong \sqrt{3 \cdot \mu_a \cdot \mu_s'}$, and $D \cong (3 \cdot \mu_s')^{-1}$. Using these approximations the ratio of Eqns. 6 and 7 becomes $$\left(\frac{\partial A}{\partial \mu_a}\right)\bigg/\left(\frac{\partial \langle t \rangle}{\partial \mu_a}\right) = \frac{-(1+\rho \cdot \mu_{\mathit{eff}}) \cdot c}{\ln 10 \left(\frac{\rho \cdot \mu_{\mathit{eff}}}{2} - \frac{\mu_a}{\mu_s'}\right)} \cdot \mu_a \qquad \text{Equation 8}$$

For media with optical properties similar to tissue, $\mu_s'=1$–$2$ mm$^{-1}$, $\mu_a=0.005$–$0.05$ mm$^{-1}$ and typical source detector distances of r=20–40 mm, $\rho \cdot \mu_{\mathit{eff}}/2 >> \mu_a/\mu_s'$ and therefore $$\left(\frac{\partial A}{\partial \mu_a}\right)\bigg/\left(\frac{\partial \langle t \rangle}{\partial \mu_a}\right) = \frac{-2 \cdot (1/\mu_{\mathit{eff}} + \rho) \cdot c}{\ln 10 \cdot \rho} \cdot \mu_a. \qquad \text{Equation 9}$$

For large source detector distances ($\rho >> 1/\mu_{\mathit{eff}}$) Eqn. 9 reduces to $$\left(\frac{\partial A}{\partial \mu_a}\right)\bigg/\left(\frac{\partial \langle t \rangle}{\partial \mu_a}\right) = \frac{-2c}{\ln 10} \cdot \mu_a, \qquad \text{Equation 10}$$

which is a linear function of $\mu_a$ and c.

Phase and Modulation Depth Quotient

The quotient $V_a = (\partial \phi / \partial \mu_a)/(\partial M/\partial \mu_a \cdot M^{-1})$ where M is the modulation depth can be derived in a similar fashion. Like $Q_a$, $V_a$ is to a good approximation a linear function of $\mu_a$. The influence of $\mu_s'$ on $V_a$ is even smaller than its influence on $Q_a$. Consequently, measuring Va gives a more precise estimate of $\mu_a$ than measuring $Q_a$.

Although the diffusion equation suggests that the $V_a$ quotient is the best to use as it is less sensitive to the scattering coefficient, it has the disadvantage that noise on the $V_a$ quotient is some 5 to 10 times larger than the $Q_a$ quotient for the same detected light intensity and measurement interval. Either a significantly larger measurement time or light intensity is required to make use of the inherent greater insensitivity of the $V_a$ quotient to $\mu_s'$.

Calculation of Hb, HbO$_2$, totHb and Saturation

A good estimate of the absolute (mean) absorption coefficient can be obtained by measuring the ratio of attenuation and phase (<t>) changes for small variations in absorption coefficient by tuning the wavelength λ, i.e. to scan over the absorption spectrum of the scattering media.

$\mu_a$ will be acquired at two different wavelengths, $\mu_1$ and $\mu_2$. This gives two equations which are solved to give [Hb] and [HbO$_2$] concentrations, $$\mu_a^{\lambda 1} = \epsilon_{Hb}^{\lambda 1} \cdot [Hb] + \epsilon_{HbO2}^{\lambda 1} \cdot [HbO_2] \qquad \text{Equation 11}$$

$$\mu_a^{\lambda 2} = \epsilon_{Hb}^{\lambda 2} \cdot [Hb] + \epsilon_{HbO2}^{\lambda 2} \cdot [HBO_2] \qquad \text{Equation 12}$$

where $\epsilon$ are extinction coefficients at the two wavelengths. Total hemoglobin is $[totHb]=[Hb]+[HbO_2]$ and Saturation is $Y_{sat}=[HbO_2]/[totHb]$.

Probe According to an Aspect of the Present Invention

Figure 2:
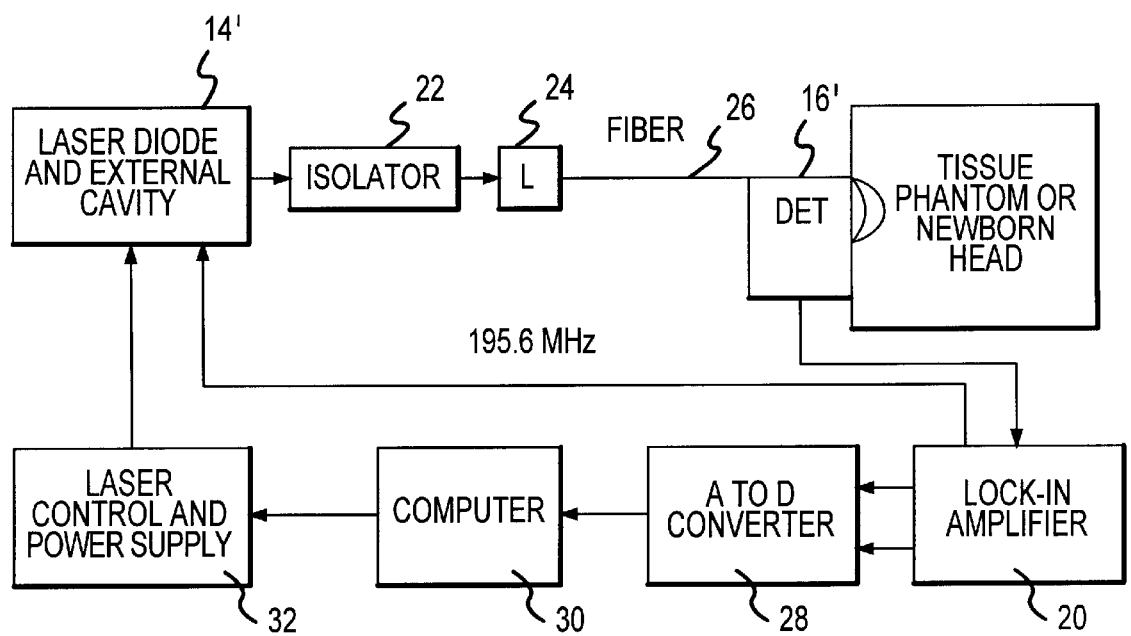
FIG. 2 is a schematic representation of a COM according to an aspect of the present invention.

A prototype Cerebral Oxygenation Monitor (COM) is shown in FIG. 2. The optical source 14' is an Environmental Optical Sensors Inc. (EOSI) 2010 tunable laser diode. The 2010 has a motorized external cavity capable of sweeping the wavelength +/−10 nm. EOSI 755 nm and 800 nm distributed feedback (DFB) laser diodes were installed to obtain respective wavelength measurements. The laser diode is amplitude modulated at 195.6 MHz with a signal from the Lock-In Amp 20. The 195.6 MHz modulation frequency was chosen because the PMT detector 16 has the best signal to noise ratio at this frequency. Each laser diode has a corresponding Optics For Research (OFR) VPO isolator 22. The laser beam was put into the fiber by an OFR Launcher 24.

A 1.0 meter OFR near infrared fiber 26 transports the light to the tissue phantom or baby head. The COM probe detector 16' is a Hamamatsu HC120 Photomultipler Tube (PMT) detector (Det) positioned 20 mm from the fiber on the tissue phantom or baby. This results in a depth penetration of 17 mm with a banana shaped optic path in the phantom or baby (see L of FIG. 1). The detector output goes to the input of the Stanford Research SR844 RF Lock-In Amplifier 20. Amplitude and phase difference of the RF modulation signal are digitized at 10 KHz with a National Instruments PCI-1200 Analog to Digital converter 28. A HP 8280 Pavilion computer 30 running Labview 5 from National Instruments controls laser wavelength and initiates data acquisition through a RS232 serial interface, connected to a Laser Control and Power Supply 32.

Another embodiment of the invention is described below with reference to FIGS. 3 and 4, wherein VCSELs are used.

Figure 3:
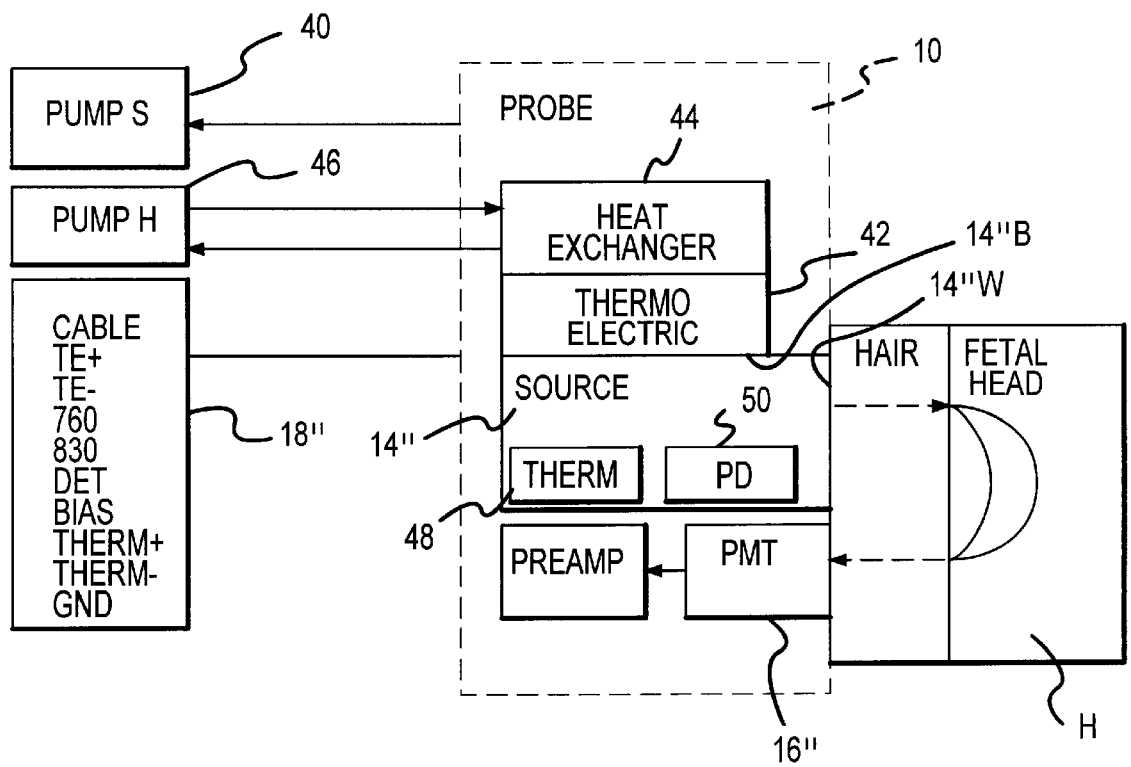
FIG. 3 is a schematic representation of another probe according to an aspect of the invention.
Figure 4:
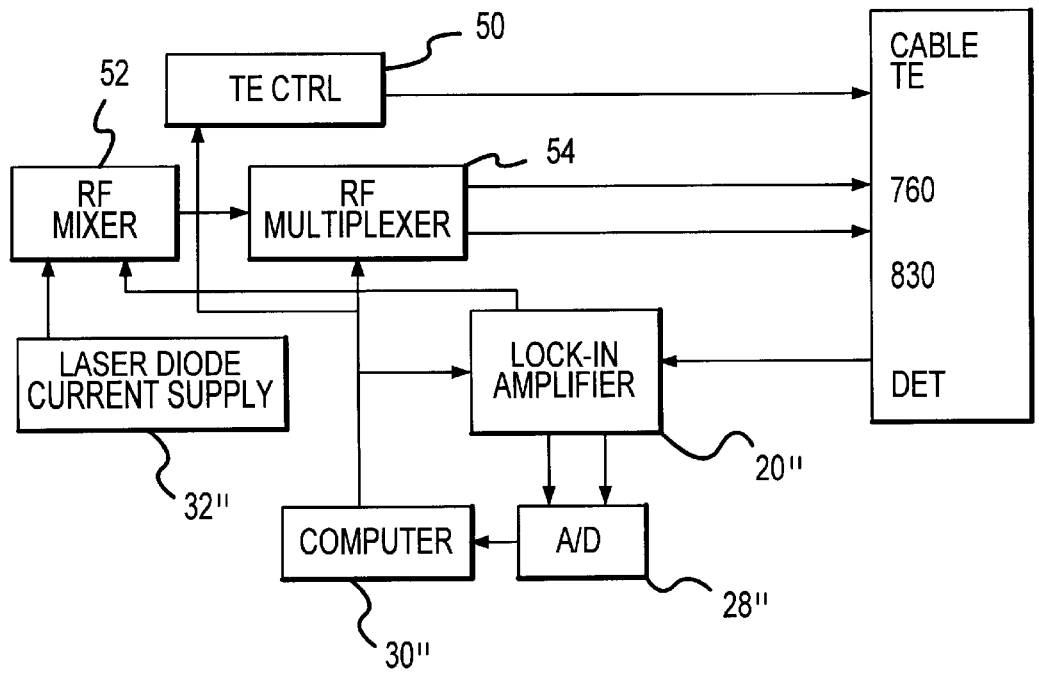
FIG. 4 is a schematic representation of the electronics associated with the probe of FIG. 3.

As shown in FIG. 3, the intrauterine probe 10 is attached to the fetal head H with a low level suction from Pump 40. (Alternatively, the probe may be attached by any other means including existing fetal monitor cables.) The detector 16" (PMT) is a Hamamatsu R5600 photomultiplier tube (PMT) with low noise preamp. The source 16" is ten 760 nm laser diodes interspersed with ten 830 nm laser diodes all enclosed in a 15 mm can. See FIG. 5. The source optical window 14"W is anti-reflective coated glass. The ceramic base 14"B of the source is fastened to a thermoelectric cooler 42. A heat sink 44 is placed on the opposite side of the cooler 42 from the laser diodes. Room air is applied by Pump 46 to the heat exchanger 44 to speed up temperature change. Thermister 48 senses laser diode temperature. Photodetector 50 provides feedback on laser diode illumination. A cable 18 transmits control and data information between the probe 10 and the electronics, which are described in connection with FIG. 4.

A thermoelectric controller 50 varies the temperature of the laser diodes 10 degrees Centigrade, which will cause a 0.2 nm change in both sets of laser diodes. The temperature is stabilized at one extreme of this temperature range to begin the measurement sequence. A RF Mixer 52 modulates the output of the laser diode current supply. The modulated current is applied to first the 760 run laser diodes for 1 second and then to the 830 nm laser diodes for 1 second through a RF Multiplexer 54. The TE controller 50 changes the temperature to the other extreme in about 9 seconds. The illuminating sequence is repeated once the temperature is stabilized. PMT detector 16" output goes to the Lock-in Amplifier 20" input. RF modulation change in amplitude and phase from the Lock-in Amplifier is digitized at 10 KHz for one second by PCI-1200 Analog to Digital Converter 28". A microprocessor 30" controls data acquisition.

Figure 5:
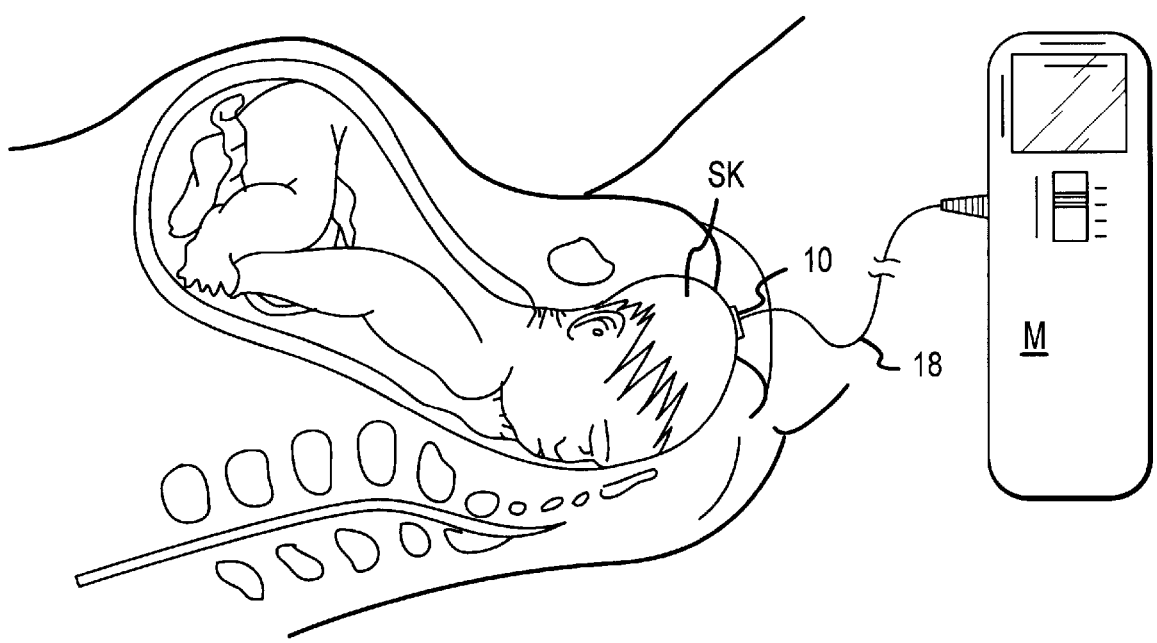
FIG. 5 is a view of the present invention showing its utility in use in a typical application.

FIG. 5 shows an operating device according to an aspect of the present invention in use in a typical application. A probe 10 is place upon the skull Sk of an intrauterine infant. The probe 10 communicates via cable 18 with a monitor M. In FIG. 5, the monitor M is part of a hand-held unit that also houses the other non-probe components, for example the components shown in FIG. 4 other than the cable 18. It should be understood that the monitor does not need to be of any particular type, and indeed represents any display device. It should also be understood that the invention is not limited to probing fetal tissue, but instead could be used to probe any tissue or other substance, including fetal tissue during pregnancy or otherwise. For example, it may be useful to probe tissue other than the brain because the body naturally protects the brain be sending it oxygen, and there may be cases where other tissue is not properly oxygenated.

Yet another aspect of the invention is a postpartum imager. The imager has a position sensor on the probe and a high resolution video display. Images will resemble diagnostic ultrasound B-scans. The technology used in the postpartum imager utilizes identical laser light sources, detectors and signal processing as any of the COM devices and methods described above. A three dimensional image is produced by overlaying many individual COM readings taken from different volumes of the newborn head on a display. The different sample volumes can be obtained in two ways. First, a source-detector pair can be positioned at different locations on the head similar to an ultrasound B-scan. Alternatively, an array of source-detector pairs can take a sequence of sample volumes similar to computed tomography.

What is claimed is:

1. A method of measuring a hemoglobin parameter comprising the steps of:
   a) projecting an amount of laser light into a skull of an intrauterine infant at a first frequency via a light source positioned on a flexible circuit capable of conforming to the skull;
   b) detecting the light projected into the skull at the first frequency via a detector positioned on a flexible circuit capable of conforming to the skull;
   c) projecting an amount of laser light into the skull at a second frequency;
   d) detecting the light projected into the skull at the second frequency; and
   e) calculating Hb and HbO2 based upon the detecting steps (b) and (d);
   wherein the projecting steps (a) and (c) use an array of VCSELs;
   f) projecting an amount of laser light into the skull at a third frequency;
   g) detecting the light projected into the skull at the third frequency;
   h) projecting an amount of laser light into the skull at a fourth frequency;
   i) detecting the light projected through the skull at the fourth frequency;
   j) calculating Hb and HbO2 based upon the detecting steps (g) and (i); and
   k) calculating a parameter based upon averaging the results of steps (e) and (j).

2. The method of claim 1, further comprising a step of calculating total Hb and Saturation.

3. The method of claim 1, wherein the calculating step (e) includes acquiring an absorption coefficient $u_a$ for the first frequency and the second frequency.

4. The method of claim 1, wherein the first frequency has a wavelength of about 755 nm and the second frequency has a wavelength of about 800 nm.

5. The method of claim 1, wherein the projecting steps (a) and (c) are performed using a light source positioned a fixed distance from the skull.

6. The method of claim 5, wherein the fixed distance is about 20 mm.

7. The method of claim 1, wherein the projecting steps (a) and (c) project light into the skull a distance of about 17 mm.

* * * * *